(12) United States Patent
Han et al.

(10) Patent No.: US 7,582,477 B2
(45) Date of Patent: *Sep. 1, 2009

(54) METHOD OF ISOLATING AND CULTURING MESENCHYMAL STEM CELL DERIVED FROM CRYOPRESERVED UMBILICAL CORD BLOOD

(75) Inventors: Hoon Han, 521-101, Hanyang APT, Yangji maeul, Soonae-dong, Boondang-gu, Seongnam-si, Gyeonggi-do (KR) 463-922; Sung-Whan Kim, Seoul (KR)

(73) Assignee: Hoon Han, Gyeonggi-Do (KR)

( * ) Notice: Subject to any disclaimer, the term of this patent is extended or adjusted under 35 U.S.C. 154(b) by 298 days.

This patent is subject to a terminal disclaimer.

(21) Appl. No.: 10/579,071

(22) PCT Filed: Oct. 25, 2004

(86) PCT No.: PCT/KR2004/002716

§ 371 (c)(1),
(2), (4) Date: May 11, 2006

(87) PCT Pub. No.: WO2005/045011

PCT Pub. Date: May 19, 2005

(65) Prior Publication Data

US 2007/0105221 A1    May 10, 2007

(30) Foreign Application Priority Data

Nov. 11, 2003   (KR) .................. 10-2003-0079363

(51) Int. Cl.
*C12N 5/00* (2006.01)
*C12N 5/02* (2006.01)

(52) U.S. Cl. .................................... 435/325
(58) Field of Classification Search ............ 435/325
See application file for complete search history.

(56) References Cited

U.S. PATENT DOCUMENTS

| | | | |
|---|---|---|---|
| 5,197,985 A | 3/1993 | Caplan et al. | |
| 5,486,359 A | 1/1996 | Caplan et al. | |
| 6,335,195 B1 | 1/2002 | Rodgers et al. | |
| 2004/0235160 A1* | 11/2004 | Nishikawa et al. | 435/370 |

2007/0092967 A1   4/2007   Han et al.

OTHER PUBLICATIONS

Erices et al., British J or Haematology, 2000, 109, 235-242.*
Office Action for U.S. Appl. No. 10/579,070 (publ. No. US 2007/0092967) dated Oct. 30, 2008.
Office Action for U.S. Appl. No. 10/579,070 (publ. No. US 2007/0092967) dated Apr. 14, 2008.
National Marrow Donor Program website, www.marrow.org, referenced for umbilical cord blood unit transplant information, accessed on Jan. 29, 2009.
New York Blood Center website, www.nationalcordbloodprogram.org, referenced for umbilical cord blood unit information, accessed on Jan. 29, 2009.
Maitra et al., Bone Marrow Transplantation 2004, 33: 597-604.
Yu et al., British Journal of Haematology 2004, 124: 666-675.
Prockop et al., Cytotherapy 2001, 3(5): 393-396.
Non-Hematopoietic Stem Cell Workshop course content, Vancouver, BC, Canada, on Sep. 28, 2008.
Cambrex catalog insert on mesenchymal stem cells, 2008.
Mareschi et al., Haematologica 2001, 86: 1099-1100.
Majumdar et al., Journal of Cell Physiology 1998, 176(1): 57-66.
Papassavas et al., International Journal of Laboratory Hematology 2008, 30, 124-132.
Romanov et al., Stem Cells 2003, 21: 105-110.
Wexler et al., British Journal of Haematology 2003, 121: 368-374.
Hou, L. et al., "Induction of Umbilical Cord Blood Mesenchymal Stem Cells into Neuron-Like Cells in Vitro", International Journal of Hematology, Oct. 2003, vol. 78 (3), pp. 256-261.
Rooney, P. & Rees, A. A., "Blood Vessel & Mesenchymal Cells: Can They Make Better Bone?" European Cells and Materials, Jun. 2003, vol. 5, Suppl. 2, p. 8.
Office Action for U.S. Appl. No. 10/579,070 (publ. No. US 2007/0092967) dated Apr. 21, 2009 and references cited therein.

* cited by examiner

*Primary Examiner*—Ruth A Davis
(74) *Attorney, Agent, or Firm*—Venable LLP; Keith G. Haddaway

(57) ABSTRACT

The present invention relates to a method of isolating and culturing mesenchymal stem cells using cryopreserved umbilical cord blood that is most ideal for cell therapy. The method comprises thawing cryopreserved umbilical cord blood and adding αMEM (alpha-minimum essential medium) thereto, followed by centrifugation to harvest monocytes; isolating CD133 positive cells from the obtained monocytes; and subjecting the isolated cells into suspension culture in the αMEM containing Stem Cell Factor, GM-CSF (granulocyte-macrophage colony-stimulating factor), G-CSF (granulocyte colony-stimulating factor), IL-3 (interleukin-3) and IL-6 (interleukin-6).

8 Claims, 2 Drawing Sheets

METHOD OF ISOLATING AND CULTURING MESENCHYMAL STEM CELL DERIVED FROM CRYOPRESERVED UMBILICAL CORD BLOOD

TECHNICAL FIELD

The present invention relates to a method of isolating and culturing a mesenchymal stem cell using umbilical cord blood that is most ideal for a cell therapy. More particularly, it pertains to a reproducible method of isolating and culturing a mesenchymal stem cell using umbilical cord blood cryoperserved at −196° C.

BACKGROUND ART

Mesenchymal stem cells refer to primitive cells that are able to differentiate into bone, cartilage, adipose tissue, nerve and muscle, etc., and are known as being contained in a large amount in bone marrow. In fact, mesenchymal stem cells are presently isolated from bone marrow and then studied for certain purposes or widely used in clinical trials for a variety of diseases.

Although it is easy to obtain mesenchymal stem cells from bone marrow, there are difficulties in acquiring bone marrow. Further, it is also difficult to solve the problems associated with an immune rejection reaction occurring when implanting stem cells to others.

Meanwhile, it is relatively easy to obtain umbilical cord blood compared with obtaining bone marrow, and also, where great numbers of umbilical cord blood units are secured, it is possible to employ umbilical cord blood stem cells that are identical with or most similar to histocompatibility genes of patients and thereby it is possible to solve the problems associated with immune rejection. However, it is relatively difficult to obtain mesenchymal stem cells from umbilical cord blood, compared with obtaining them from bone marrow and thereby there is difficulty in study and clinical applications.

Conventionally, there has been largely used a method of separating and culturing mesenchymal stem cells from umbilical cord blood within 24 hours from birth, using a density gradient centrifugation method. However, when the density gradient centrifugation method is applied to cryopreserved umbilical cord blood, it is difficult to separate cells and easy to lose cells, which makes it more difficult to culture mesenchymal stem cells that are present in umbilical cord blood in a minute amounts.

As conventional methods of isolating and culturing mesenchymal stem cells, reference is made to U.S. Pat. Nos. 5,197,985 and 5,486,359, which disclose a method of proliferating mesenchymal stem cells in isolating and culturing mesenchymal stem cells from human bone marrow. That is, U.S. Pat. No. 5,197,985 is directed to a method for inducing human bone marrow-derived mesenchymal stem cells to differentiate into bone-forming cells, comprising: providing human bone marrow-derived mesenchymal stem cells that have been isolated, purified and culturally expanded from a bone marrow specimen by adding the bone marrow specimen to a medium which contains factors which stimulate mesenchymal cell growth without differentiation and allows, when cultured, for selective adherence of only the mesenchymal stem cells to a substrate surface; applying the isolated, purified and culturally expanded human bone marrow-derived mesenchymal stem cells to a porous carrier; and, implanting the porous carrier containing the culturally expanded human bone marrow-derived mesenchymal stem cells into an environment containing factors necessary for differentiating the human mesenchymal stem cells into bone cells. In the method, the porous carrier comprises hydroxyapatite and tricalcium phosphate and the medium is comprised of $BGJ_b$ medium with fetal bovine serum (FBS) or is comprised of F-12 Nutrient Mixture. Further, U.S. Pat. No. 5,486,359 discloses isolated human mesenchymal stem cells which can differentiate into cells of more than one tissue type (for example, bone, cartilage, muscle or marrow stroma), a method for isolating, purifying and culturally expanding human mesenchymal stem cells, and characterization and uses thereof, particularly research reagent, diagnostic and therapeutical uses of such cells. In the patent, mesenchymal stem cells are derived from bone marrow and cultured in $BGJ_b$ medium containing fetal bovine serum.

DISCLOSURE OF INVENTION

Technical Problem

Therefore, the present invention has been made in view of the above problems raised in culturing mesenchymal stem cells, and it is an object of the present invention to provide a reproducible method of isolating and culturing mesenchymal stem cells, in which mesenchymal stem cells can be obtained from umbilical cord blood cryopreserved at −196° C. without the loss of cells in the course of density gradient centrifugation.

Technical Solution

In accordance with an aspect of the present invention, there is provided a method of isolating and culturing mesenchymal stem cells from cryopreserved umbilical cord blood, comprising the steps of:

thawing cryopreserved umbilical cord blood and adding αMEM (alpha-minimum essential medium) thereto, followed by centrifugation to harvest monocytes;

isolating CD133 positive cells from the obtained monocytes; and subjecting the isolated cells into suspension culture in the αMEM containing Stem Cell Factor, GM-CSF (granulocyte-macrophage colony-stimulating factor), G-CSF (granulocyte colony-stimulating factor), IL-3 (interleukin-3) and IL-6 (interleukin-6).

The present invention provides a reproducible method of isolating and culturing mesenchymal stem cells from umbilical cord blood units cryopreserved at −196° C. That is, it is intended to contribute to treatment of intractable diseases using umbilical cord blood, by finding out optimum conditions for isolating and culturing mesenchymal stem cells from umbilical cord blood relatively lacking the number of cells.

In order to achieve this purpose, the present invention is completed by obtaining monocytes from cryopreserved umbilical cord blood, isolating CD133 positive cells, and then culturing the cells in αMEM including Stem Cell Factor, GM-CSF, G-CSF, IL-3 and IL-6, thereby making it possible to secure primitive mesenchymal stem cells and improve the success rate of cell culture. It is difficult to isolate monocytes from cryopreserved umbilical cord blood that contains red blood cells mixed with monocytes. Therefore, it is necessary to select and culture CD133 positive cells that is presumed to contain stem cells. According to the process of the present invention, the success rate of cell culture is up to about 90%. No case is reported that stem cells are cultured from cryopreserved umbilical cord blood or bone marrow in the conventional method.

DESCRIPTION OF THE DRAWINGS

The above and other objects, features and other advantages of the present invention will be more clearly understood from the following detailed description taken in conjunction with the accompanying drawings, in which.

BEST MODE

Figure 1:
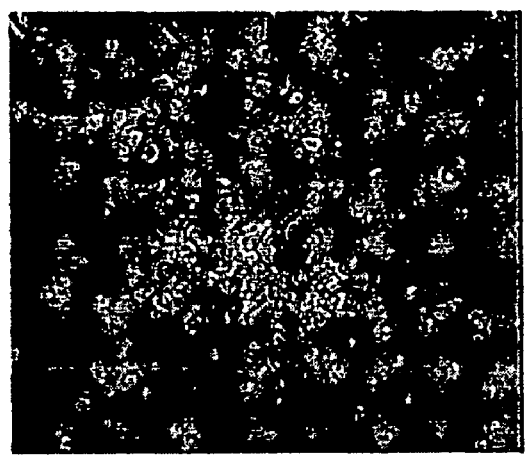
FIGS. 1 through 6, respectively, are photographs (×100) showing results after culturing mesenchymal stem cells derived from cryopreserved umbilical cord blood for 5, 7, 10, 14, 20 and 25 days, in accordance with the method of the present invention.

Hereinafter, a method of isolating and culturing mesenchymal stem cells from cryopreserved umbilical cord blood in accordance with the present invention will be described in more detail with reference to the following Examples. These examples are provided only for illustrating the present invention and should not be construed as limiting the scope and spirit of the present invention.

EXAMPLES

Example 1

Isolation and Culture of Mesenchymal Stem Cells

Umbilical cord blood units cryopreserved at −196° C. was thawed in water bath at 37° C. In order to isolate monocytes from the umbilical cord blood, the umbilical cord blood was diluted with two-fold volume of αMEM (alpha-minimum essential medium, Jeil Biotech Services, Korea) and was centrifuged at 300×g for 10 minutes at room temperature. The separated buffy coat layer was collected, diluted again with two-fold volume of αMEM, overlapped on Ficoll-Hypaque and centrifuged at 300×g for 30 minutes at room temperature.

In separating monocytes from blood, Ficoll-Hypaque, which is a polymer of Ficoll (sucrose polymer) and Hypaque (sodium ditrizoate), is largely used. Ficoll-Hypaque has a specific gravity of 1.077 g/ml, which is heavier than monocytes, but lighter than red blood cells, which makes it possible to separate the cells from each other by specific gravity difference therebetween. That is, when blood is placed on Ficoll-Hypaque and centrifuged, monocytes are gathered on Ficoll-Hypaque.

Monocytes obtained by density gradient centrifugation method were washed twice with a washing αMEM in which additives were not included.

From the obtained monocytes, CD133 positive cells were selected with Isolation kit (Miltenyi Bioteck, Germany) as follows: monocytes were added with 100 μl of blocking reagent to remove non-specific bonding, and then mixed with 100 μl of CD133/Microbead. The mixture was cultured at 4° C. for 30 minutes. The culture was added with ten-fold volume of PBS (D-phosphate buffered saline, Jeil Biotech Services, Korea), centrifuged at 300×g for 10 minutes, and thereafter, PBS was discarded to obtain the cells adhered to the tube. The cells were resuspended with 500 μl of PBS. After the column of Isolation kit was washed with 3 ml of PBS, the resuspended cells were loaded and maintained in the column more than 15 minutes. The column, after rinsed with PBS four times, was removed from the kit and then added with PBS in a tube, followed by flushed with plunger to select positive cells.

Next, 20% fetal bovine serum (FBS, Jeil Biotech Services, Korea), Stem Cell Factor (50 ng/ml), GM-CSF (granulocyte-macrophage colony-stimulating factor; 10 ng/ml), G-CSF (granulocyte colony-stimulating factor; 10 ng/ml), IL-3 (interleukin-3; 10 ng/ml) and IL-6 (interleukin-6; 10 ng/ml) were added to αMEM containing antibiotics (1000 U/ml of penicillin G, 1000 μg/ml of streptomycin sulfate, Gibco-BRL), an anti-fungal agent (0.25 μg/ml amphotericin B) and 2 mM of Glutamine (Sigma) and the selected cells were suspended in the concentration of $1 \times 10^6/cm^2$.

After five-days culturing, suspending cells were removed from the cultured cell group. When adherent cells were secured, they were cultured for 25 days in αMEM containing 20% fetal bovine serum and antibiotics, with complete replacement of culture medium at intervals of 2 days without washing process.

Figure 2:
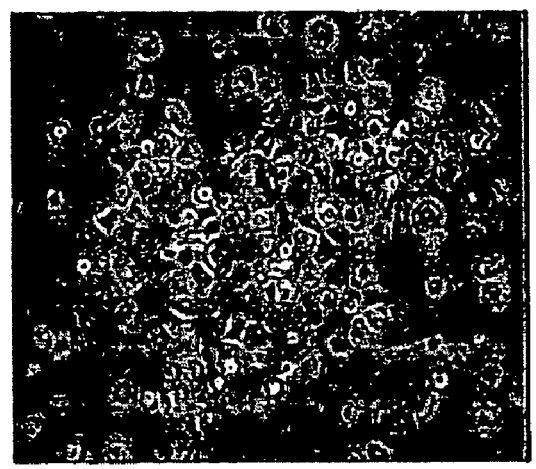
Figure 3:
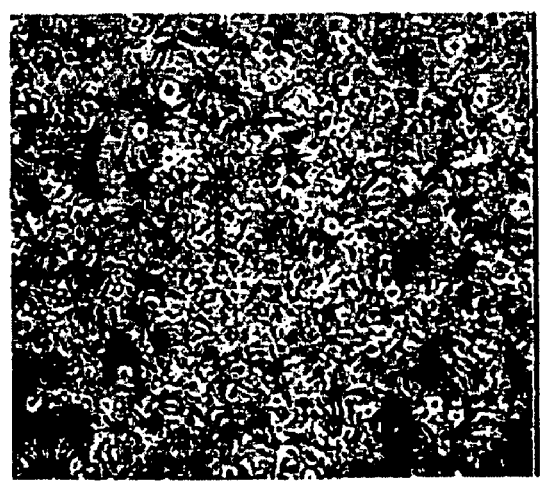
Figure 4:
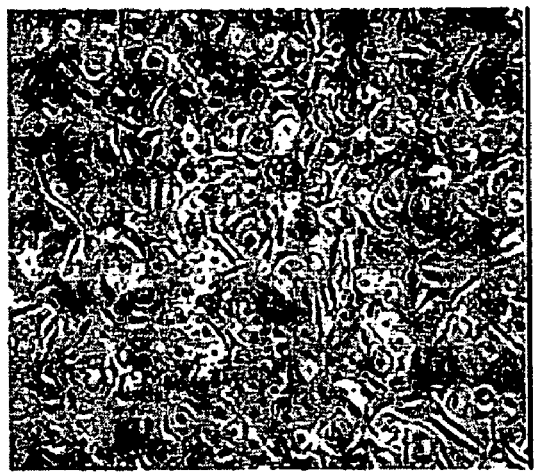
Figure 5:
Figure 6:

FIGS. 1 through 6, respectively, are photographs (×100) showing results after culturing mesenchymal stem cells derived from cryopreserved umbilical cord blood for 5, 7, 10, 14, 20 and 25 days, in accordance with the method of the present invention. As shown in the figures, when monocytes isolated from umbilical cord blood were cultured, cells adhered to and growing at the bottom of the flask were observed 5 days after culturing and on the $7^{th}$ day, cells formed colonies and then grown to cells having various shapes. 10 days after culturing, monocytes undergoes differentiation into spindle-shaped cells, and 25 days after culturing, these spindle-shaped cells become complete mesenchymal stem cells through cell division and multiplification, thereby completing culturing.

Example 2

Characterization of Cell Surface Antigen of Cultured Mesenchymal Stem Cells

In order to determine the characteristics of cell surface antigen of the spindle-shaped mesenchymal stem cells isolated and cultured as described above, the cell surface antigen was analyzed by FACS. The results are shown in Table 1 below. FACS (fluorescence activated cell sorting; a flow cytometer) is used to analyze the characteristics of cells by attaching a luminescent immune antigen indicator to the surface thereof, or to separate cells containing a certain antigen indicator depending.

TABLE 1

| Indicator | Reaction |
|---|---|
| CD14 | − |
| CD34 | − |
| CD45 | − |
| SH2 | + |
| SH3 | + |
| CD29 | + |
| CD44 | + |
| CD90 | + |
| CD166 | (+) |

As shown in Table 1, the stem cells isolated and cultured in accordance with the present invention show negative reaction in CD34, CD45 and CD14, which are characteristic indicator of hematopoietic stem cells, positive reaction in SH2, SH3, CD29 and CD44, which are characteristic indicator of mesenchymal stem cells, and weak positive reaction in CD166.

Accordingly, it is confirmed that the cells isolated and cultured in accordance with the present invention are mesenchymal stem cells.

Example 3

Comparison of Success Rate of Mesenchymal Stem Cell Culture 50 units of cryopreserved umbilical cord blood were cultured according to a conventional method and the method of the present invention, and success rates of cell culture were compared therebetween. The results are shown in Table 2 below.

TABLE 2

|  | Conventional method | Inventive method |
|---|---|---|
| Number of mesenchymal stem cell units acquired | 0 | 49 |
| Success rate of culturing (%) | 0 | 98 |

As shown in Table 2, the success rate of mesenchymal stem cell culture of the conventional method is 0%, while that of the present invention is a high success rate of 98%.

INDUSTRIAL APPLICABILITY

As described above, in accordance with the present invention, it is possible to effectively isolate and culture mesenchymal stem cells from umbilical cord blood relatively lacking the number of cells, and therefore, umbilical cord blood which is wastefully disposed may be utilized as important means for treating a variety of intractable diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of isolating and culturing mesenchymal stem cells from cryopreserved umbilical cord blood, comprising the steps of:
   thawing cryopreserved umbilical cord blood and adding alpha-minimum essential medium (αMEM) thereto, followed by centrifugation to harvest monocytes;
   isolating CD133 positive cells from the obtained monocytes; and
   suspending the isolated cells into culture with αMEM containing at least one of Stem Cell Factor, granulocyte-macrophage colony-stimulating factor (GM-CSF), granulocyte colony-stimulating factor (G-CSF), interleukin-3 (IL-3) and interleukin-6 (IL-6).

2. The method as set forth in claim 1, wherein the umbilical cord blood is added with 2-fold volume of the αMEM, overlapped on Ficoll-Hypaque, and then subjected to centrifugation to harvest monocytes.

3. The method as set forth in claim 1, wherein the αMEM for culturing monocytes further comprises at least one of an antibiotic, an anti-fungal agent, glutamine and fetal bovine serum.

4. The method as set forth in claim 3, wherein the αMEM for culturing monocytes further comprises an antibiotic, an anti-fungal agent, glutamine and fetal bovine serum.

5. The method of claim 3, wherein the antibiotic is selected from penicillin G, streptomycin sulfate, or a combination thereof.

6. The method of claim 3, wherein the antifungal agent is amphotericin B.

7. The methods set forth in claim 1, wherein the culture in the αMEM contains Stem Cell Factor, GM-CSF, G-CSF, IL-3 and IL-6.

8. The method of claim 1, wherein the isolated mesenchymal stem cells are negative for CD14, CD34, CD45 indicators and are positive for SH2, SH3, C29, CD44, CD90, and CD166 indicators.

* * * * *

UNITED STATES PATENT AND TRADEMARK OFFICE
CERTIFICATE OF CORRECTION

PATENT NO. : 7,582,477 B2 Page 1 of 1
APPLICATION NO. : 10/579071
DATED : September 1, 2009
INVENTOR(S) : Han et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 411 days.

Signed and Sealed this

Fourteenth Day of December, 2010

David J. Kappos
*Director of the United States Patent and Trademark Office*